United States Patent

Huebner

[11] Patent Number: 5,810,825
[45] Date of Patent: Sep. 22, 1998

[54] SURGICAL WIRE CLAMP

[76] Inventor: Randall J. Huebner, 10950 SW. 5th St., Suite 170, Beaverton, Oreg. 97005

[21] Appl. No.: 457,624
[22] Filed: Jun. 1, 1995
[51] Int. Cl.$^6$ ................................................. A61B 17/56
[52] U.S. Cl. ............................................. 606/74; 606/103
[58] Field of Search ............................ 606/72, 74, 103; 24/122.6, 122.7, 129 B, 115 M, 130

[56] References Cited

U.S. PATENT DOCUMENTS

| | | |
|---|---|---|
| 76,141 | 3/1868 | Barnum . |
| 190,641 | 5/1877 | Stouffer . |
| 866,144 | 9/1907 | Kobert ........................ 24/126 |
| 2,171,524 | 9/1939 | Gates ............................ 24/28 |
| 2,276,571 | 3/1942 | Grypma ..................... 24/129.8 |
| 2,464,432 | 3/1949 | Brickman ..................... 140/11 |
| 2,986,787 | 6/1961 | Ackermann .................... 24/28 |
| 3,641,629 | 2/1972 | Beardsley ...................... 24/23 |
| 3,754,303 | 8/1973 | Pollock ......................... 24/23 |
| 4,473,925 | 10/1984 | Jansen ......................... 24/23 |
| 4,527,308 | 7/1985 | Tritton et al. ............. 24/115 M |
| 4,790,303 | 12/1988 | Steffee ....................... 128/924 |
| 4,896,668 | 1/1990 | Popoff et al. ................. 606/74 |
| 5,051,543 | 9/1991 | McGuire ....................... 174/78 |
| 5,190,545 | 3/1993 | Corsi et al. ................... 606/74 |
| 5,312,410 | 5/1994 | Miller et al. ................. 606/103 |
| 5,356,412 | 10/1994 | Golds et al. .................. 606/74 |

Primary Examiner—Michael Buiz
Assistant Examiner—Patrick W. Rasche
Attorney, Agent, or Firm—Marger, Johnson, McCollom & Stolowitz

[57] ABSTRACT

A surgical wire clamp assembly including a body and a wire. The wire is preferably a monofilament wire. The body includes a first longitudinal bore for receiving a first wire end, a second longitudinal bore for receiving a second wire end, and a vertical opening between the longitudinal bores. The longitudinal bores are deformable to a serpentine configuration responsive to a transverse compressive force.

4 Claims, 2 Drawing Sheets

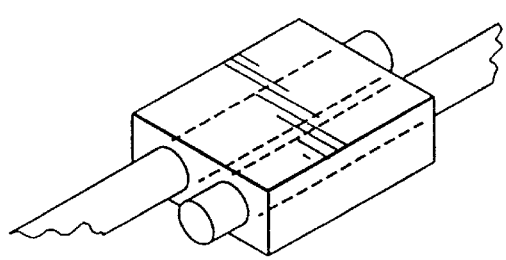
FIG.1 PRIOR ART
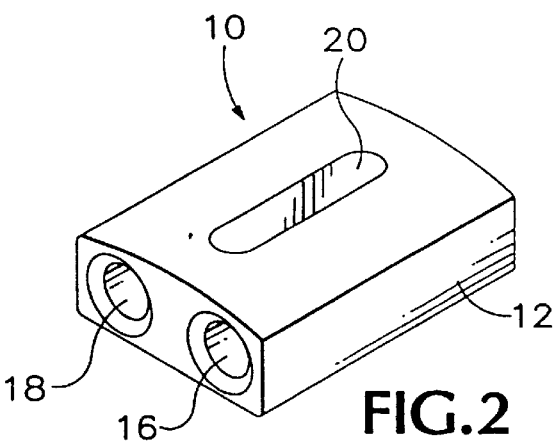
FIG.2
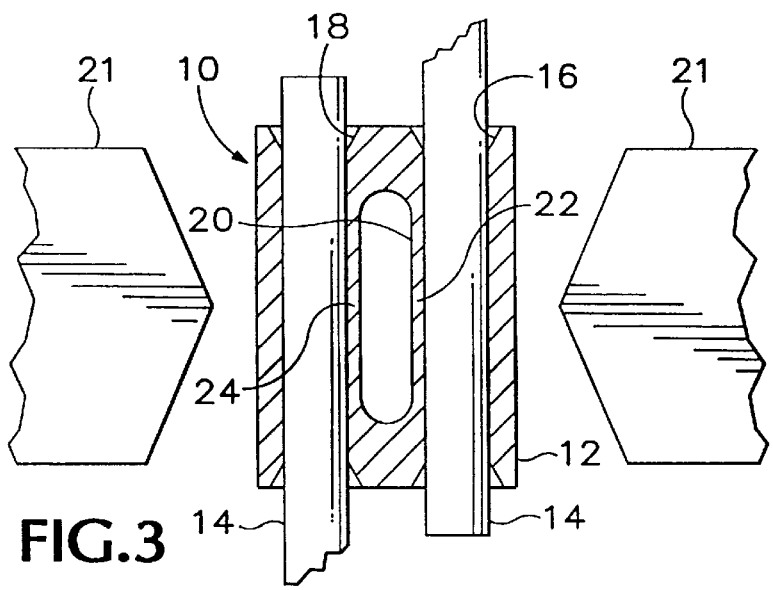
FIG.3
FIG.4
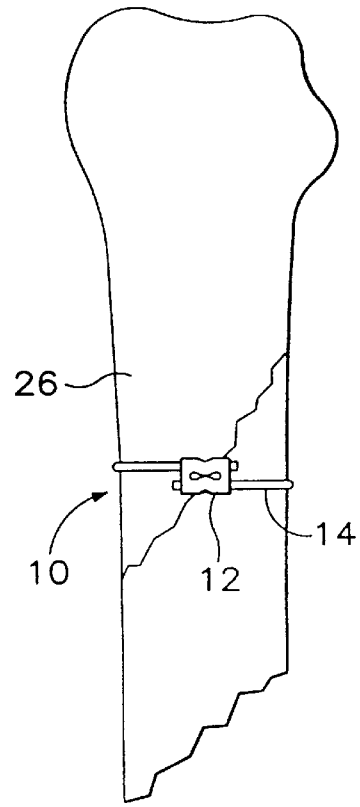
FIG.5

5,810,825

SURGICAL WIRE CLAMP

BACKGROUND OF THE INVENTION

The present invention relates to repairing split or fractured bones, and in particular, to a wire and sleeve assembly for securing together portions of a fractured bone to facilitate healing.

It is routine surgical practice to bind portions of a fractured bone together to ensure their proper alignment and to facilitate the knitting together of the bone portions. Wire and clamp assemblies are typically used for this purpose. Such assemblies can be subjected to very high tensile forces when, for example, the fractured bone is subjected to a high bending moment. It is therefore important that the wire and clamp assembly embody the highest possible resistance to tensile forces which may cause such failures.

Known wire and clamp assemblies, as exemplified in FIG. 1, include a stranded, stainless steel cable and a sleeve having a pair of bores to receive the ends of the cable. Each cable end is clamped in one bore by urging the outer wall of the bore against the cable, squeezing the cable between the outer wall of the bore and the solid central portion of the sleeve. While such wire and clamp assemblies perform satisfactorily in most cases, they sometimes fail under high bending forces exerted on the fractured bone as described above. Moreover, the stranded stainless steel wire used in such assemblies is relatively expensive. A need therefore remains for a stronger, less expensive wire and clamp assembly for binding fractured bones.

SUMMARY OF THE INVENTION

The surgical wire clamp of the present invention comprises a wire locking sleeve and a wire. The sleeve has two longitudinal bores and a medial vertical opening. Either longitudinal bore may extend part or all the way through the body. The vertical opening and the first and second longitudinal bores are separated by respective first and second longitudinal walls. In one embodiment of the invention, the first and second longitudinal bores communicate with the vertical bore. The body around each longitudinal bore is deformable into a serpentine configuration for interlockingly engaging portions of the wire disposed therein. Deformation of the body around the longitudinal bores (and the attendant deformation of the longitudinal wall) is achieved by applying a transverse compressive force to the sleeve.

In another embodiment, the wire has a first end portion connected to the sleeve, and a second distal portion. A longitudinal bore is formed in the sleeve, and has a first configuration adapted for slidingly receiving the second distal portion of the wire. A vertical bore is formed in the sleeve adjacent the longitudinal bore. The body around the longitudinal bore is deformable to a serpentine configuration for interlockingly engaging the second portions of the wire responsive to a compressive force applied transversely against the body.

The invention is also embodied in a method of connecting a wire which includes the steps of providing a sleeve, forming first and second longitudinal bores through the clamp body, and forming a vertical opening in the body between the first and second longitudinal bores. The ends of the wire are inserted into the respective first and second longitudinal bores. The body around the first and second longitudinal bores and the wire ends are then deformed into serpentine configurations, clamping the respective first and second wire portions in the clamp body. The step of deforming the first and second longitudinal bores into a serpentine configuration may include applying a transverse compressive force to the clamp body, and may further include the step of inwardly deforming the first and second walls of the vertical opening.

The invention is also embodied in a method of supporting a fractured bone which further includes the step of passing a wire around the fractured bone before inserting the first and second wire ends into the respective first and second longitudinal bores.

In each embodiment of the invention, the wire is preferably a stainless steel, monofilament wire, but can also include a stranded wire of stainless steel or other suitable materials.

The invention will now be described in greater detail by reference to the drawings.

BRIEF DESCRIPTION OF THE DRAWINGS

FIG. 1 is a perspective view of a prior art surgical wire clamp assembly.

FIG. 2 is perspective view of one embodiment of a surgical wire clamp sleeve according to the present invention.

FIG. 3 is a cutaway plan view of the surgical wire clamp of FIG. 2 having first and second ends of the surgical wire inserted into the respective first and second longitudinal bores.

FIG. 4 is a cutaway plan view of a wire and clamp assembly shown in FIG. 3 wherein the longitudinal bores, longitudinal walls, and the wire ends have been deformed into interlocking serpentine configurations.

FIG. 5 is a top view of a wire and clamp assembly according to the present invention which has been applied to stabilize a fractured bone.

DETAILED DESCRIPTION

Figure 6:
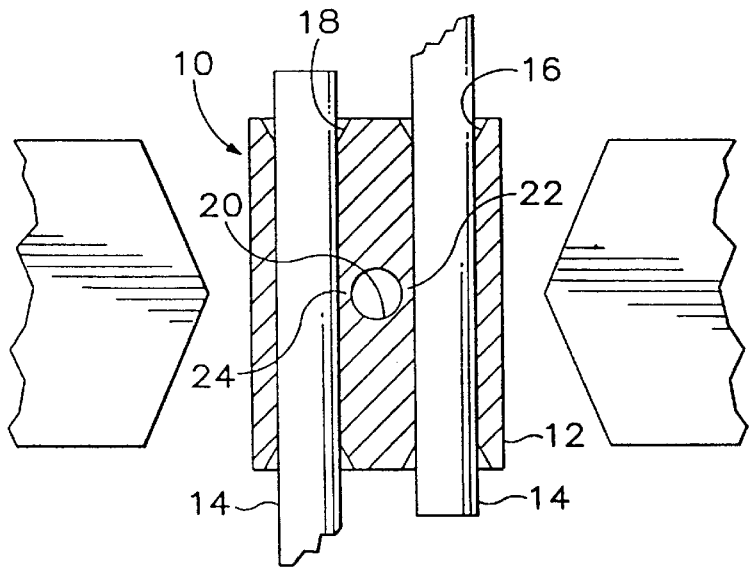
FIG. 6 is a cutaway plan view of an alternative embodiment of the surgical wire clamp assembly having a circular opening.
Figure 7:
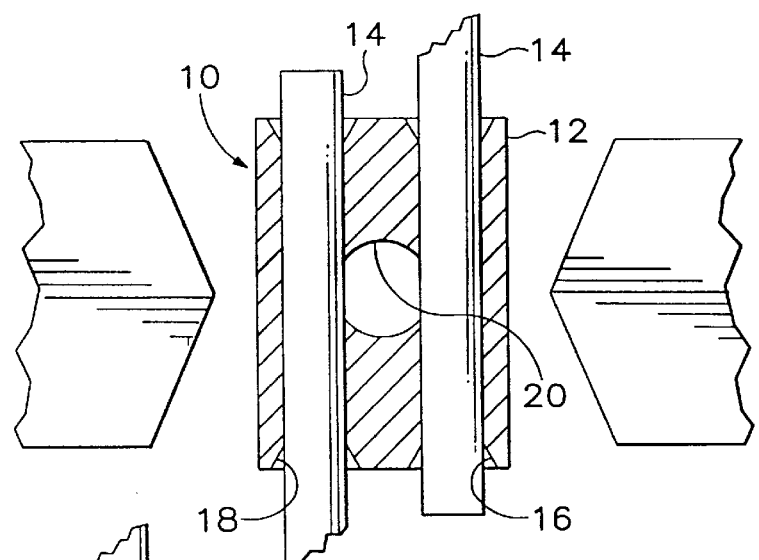
FIG. 7 is a cutaway plan view of an alternative embodiment of the surgical wire clamp assembly where the circular opening communicates with the longitudinal bores.
Figures 8, 9, 10:
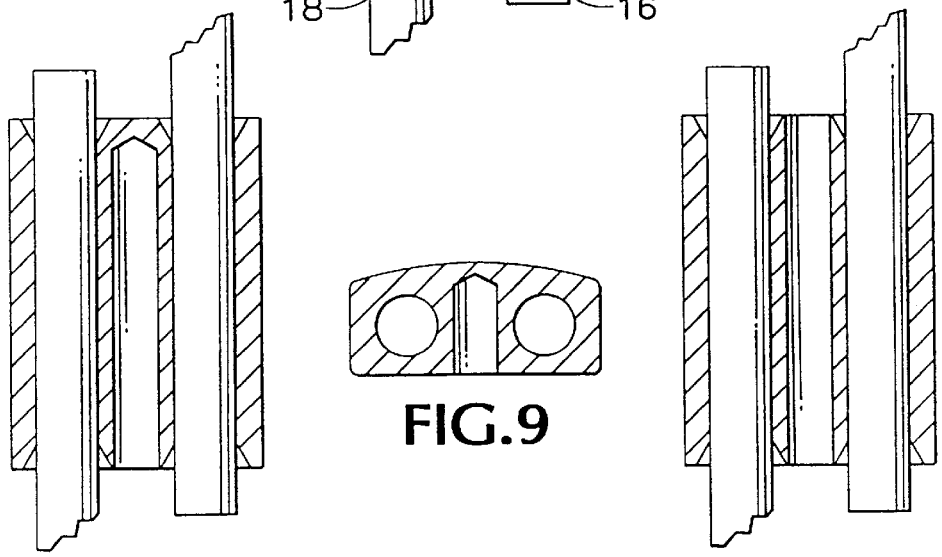
FIG. 8 is a cutaway plan view of an alternative embodiment of the surgical wire clamp assembly where the central opening is a blind longitudinal bore.
FIG. 9 is a sectional elevational view of an alternative embodiment of the surgical wire claim assembly where the central opening is a blind vertical bore.
FIG. 10 is a cutaway plan view of an alternative embodiment of the surgical wire clamp assembly where the central opening is a through longitudinal bore.

Referring now to FIGS. 2-7, a surgical wire clamp 10 according to the present invention includes body 12 and wire 14. Body 12 includes longitudinal bores 16 and 18, which preferably extend through the body. In alternative embodiments, either or both of longitudinal bores 16 and 18 may be blind bores which do not extend through body 12. Vertical opening 20 extending through body 12 is preferably located between longitudinal bores 16 and 18, and is round as shown in FIGS. 6 and 7. In alternative embodiments, opening 20 may be shaped differently, including but not limited to the oblong (shape shown in FIG. 3). Opening 20 may extend only partially through body 12. In the embodiments shown in FIGS. 2–6, vertical opening 20 and longitudinal bores 16 and 18 together define walls 22 and 24 respectively. Wire 14 is a surgical grade wire, typically of stainless steel. In the preferred embodiment, wire 14 is monofilament for reasons described below, but may also be stranded.

Surgical wire clamp 10 is applied by passing wire 14 around fractured bone 26 in FIG. 5, inserting the wire ends into longitudinal bores 16 and 18, and then drawing them tight. (FIGS. 3, 5). Pliers 21 having pointed jaws are then squeezed against body 12 to deform longitudinal bores 16 and 18 and the wire ends into interlocking, serpentine configurations (FIG. 4). Deformation of the body surrounding the longitudinal bores into a serpentine bore configuration is made possible by opening 20, which allows deformation of walls 22 and 24. The serpentine bore configuration achieved with the present invention provides greater clamping forces than has heretofore been possible with prior art clamps in which only the outer wall of each longitudinal bore is urged against the stranded wire, but in which the inner wall of the bore is not deformable by any level of compressive forces which can be readily applied in a surgical setting.

Applicant has also discovered that use of a monofilament, stainless steel surgical wire in conjunction with the serpentine configuration increases the strength of the wire clamp assembly even further. Increased strength is achieved by using a monofilament wire for at least two reasons. First, the stainless steel monofilament wire undergoes plastic deformation as it is deformed into its serpentine configuration. If the deformed monofilament wire is to be pulled from the body, sufficient force must be applied to rework the wire as it is passes through the serpentine bore. Reworking the wire is particularly difficult because the wire was work-hardened during its initial deformation. Stranded wire on the other hand, is more resilient, and does not plastically deform or work-harden as much as monofilament wire when urged into the serpentine configuration achieved in the present invention. As a result, stranded wire can be separated from the body by a lesser force than that required for monofilament wire. Moreover, this greater strength achieved by use of monofilament wire is achieved at lower overall cost due to its lower cost compared to stranded stainless steel wire.

In an alternative embodiment (not shown), the surgical clamp comprises body 12 and wire 14 having a first end permanently fixed in bore 16, and a second distal end. Body 12 has a longitudinal bore 18 to receive the distal end of wire 14. In use, the distal end of wire 14 is passed around the fractured bone and inserted into bore 18. Bore 18 and the second wire end are then deformed into an interlocking, serpentine configuration by use of a plier as described above. This embodiment provides the advantage of having only one portion of the wire which is slidable relative to the body, rendering installation easier in some instances.

The foregoing description of the preferred embodiments of the invention are illustrative rather than exhaustive. Those skilled in the art will recognize that modifications in details and materials can be made without departing from the scope of the following claims.

I claim:

1. A method of supporting a fractured bone comprising the steps of:

providing a sleeve having a longitudinal dimension, a transverse dimension, a vertical dimension, first and second longitudinal bores, and an opening located medially of the first and second longitudinal bores;

passing a monofilament wire around the fractured bone;

inserting first and second wire portions into the first and second longitudinal bores respectively; and deforming the sleeve between the first and second longitudinal bores, the wire portions contained therein, and the medial opening into interlocking configurations until the first and second wire portions are interlockingly engaged in the respective first and second bores.

2. The method of claim 1 wherein the step of deforming the sleeve between the first and second longitudinal bores and the wire portions contained therein comprises applying a transverse compressive force to the sleeve.

3. The method of claim 2 wherein the step of deforming the first and second longitudinal bores and the wire portions contained therein into interlocking configurations includes the step of deforming the transverse walls of the first and second bores toward the opening.

4. The method of claim 3 wherein the step of applying a transverse compressive force to the sleeve comprises applying a maximum amount of force at substantially the midpoint of the sleeve.

\* \* \* \* \*